(12) United States Patent
Hushka (10) Patent No.: US 7,686,827 B2
(45) Date of Patent: Mar. 30, 2010

(54) MAGNETIC CLOSURE MECHANISM FOR HEMOSTAT

(75) Inventor: Dylan Hushka, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 962 days.

(21) Appl. No.: 11/255,843

(22) Filed: Oct. 21, 2005

(65) Prior Publication Data
US 2006/0089670 A1 Apr. 27, 2006

Related U.S. Application Data

(60) Provisional application No. 60/620,805, filed on Oct. 21, 2004.

(51) Int. Cl.
*A61B 17/00* (2006.01)
(52) U.S. Cl. ..................................... 606/208
(58) Field of Classification Search ................ 606/157, 606/120, 205, 206, 208; 433/159; 81/300–427.5
See application file for complete search history.

(56) References Cited

U.S. PATENT DOCUMENTS

| | | | |
|---|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,279,753 A | 4/1942 | Knopp |
| 2,305,156 A | 12/1942 | Grubel |
| 2,632,661 A | 3/1953 | Cristofv |
| 2,668,538 A | 2/1954 | Baker |
| 2,796,065 A | 6/1957 | Kapp |
| 3,417,752 A | 12/1968 | Butler |
| 3,459,187 A | 8/1969 | Pallotta |

(Continued)

FOREIGN PATENT DOCUMENTS

CA 2104423 2/1994

(Continued)

OTHER PUBLICATIONS

Int'l Search Report EP 05016399 dated Jan. 5, 2006.

(Continued)

*Primary Examiner*—Todd E Manahan
*Assistant Examiner*—Michael G Mendoza (57) ABSTRACT

A hemostat includes a housing which has a shaft extending distally therefrom. The shaft has an end effector assembly distally attached thereto. The hemostat also includes a pair of first and second handles which are connected to the housing. The first and second handles are operatively connected to the end effector assembly. At least one of the first and second handles are moveable relative to the other handle to effectively actuate the end effector assembly. The hemostat further includes a magnetic closure mechanism which has a first magnet connected to the first handle and a second magnet connected to the second handle. The first and second magnets each have a magnetic potential and are securely engageable with one another when the handles are moved from a first spaced configuration to a second closer position.

17 Claims, 4 Drawing Sheets

U.S. PATENT DOCUMENTS

| | | |
|---|---|---|
| 3,643,663 A | 2/1972 | Sutter |
| 3,651,811 A | 3/1972 | Hildebrandt et al. |
| 3,720,896 A | 3/1973 | Beierlein |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,233,734 A | 11/1980 | Bies |
| 4,300,564 A | 11/1981 | Furihata |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,215 A | 4/1987 | Pike |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,846,171 A | 7/1989 | Kauphusman et al. |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,035,695 A | 7/1991 | Weber, Jr. et al. |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,151,978 A * | 9/1992 | Bronikowski et al. ....... 709/216 |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,314,445 A | 5/1994 | Degwitz et al. |
| 5,318,589 A | 6/1994 | Lichtman |
| 5,324,289 A | 6/1994 | Eggers |
| 5,326,806 A | 7/1994 | Yokoshima et al. |
| 5,330,471 A | 7/1994 | Eggers |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,376,089 A | 12/1994 | Smith |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |

| Patent | Date | Inventor |
|---|---|---|
| 5,542,945 A | 8/1996 | Fritzsch |
| 5,558,671 A | 9/1996 | Yates |
| 5,558,672 A | 9/1996 | Edwards et al. |
| 5,562,699 A | 10/1996 | Heimberger et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,805 A | 11/1996 | Li |
| 5,578,052 A | 11/1996 | Koros et al. |
| 5,582,611 A | 12/1996 | Tsukagoshi et al. |
| 5,585,896 A | 12/1996 | Yamazaki et al. |
| 5,590,570 A | 1/1997 | LeMaire, III et al. |
| 5,603,711 A | 2/1997 | Parins et al. |
| 5,603,723 A | 2/1997 | Aranyi et al. |
| 5,611,798 A | 3/1997 | Eggers |
| 5,620,453 A | 4/1997 | Nallakrishnan |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,658,281 A | 8/1997 | Heard |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,681,282 A | 10/1997 | Eggers et al. |
| 5,688,270 A | 11/1997 | Yates et al. |
| 5,693,051 A | 12/1997 | Schulze et al. |
| 5,695,522 A | 12/1997 | LeMaire, III et al. |
| 5,700,261 A | 12/1997 | Brinkerhoff |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,755,717 A | 5/1998 | Yates et al. |
| 5,766,130 A | 6/1998 | Selmonosky |
| 5,766,166 A | 6/1998 | Hooven |
| 5,766,170 A | 6/1998 | Eggers |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,701 A | 7/1998 | McBrayer et al. |
| H1745 H | 8/1998 | Paraschac |
| 5,792,137 A | 8/1998 | Carr et al. |
| 5,792,177 A | 8/1998 | Kaseda |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,817,093 A | 10/1998 | Williamson, IV et al. |
| 5,820,630 A | 10/1998 | Lind |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,860,976 A | 1/1999 | Billings et al. |
| 5,876,401 A | 3/1999 | Schulze et al. |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,984 A | 7/1999 | Sutcu et al. |
| 5,925,043 A | 7/1999 | Kumar et al. |
| 5,935,126 A | 8/1999 | Riza |
| 5,944,718 A | 8/1999 | Dafforn et al. |
| 5,951,549 A | 9/1999 | Richardson et al. |
| 5,954,720 A | 9/1999 | Wilson et al. |
| 5,957,923 A | 9/1999 | Hahnen et al. |
| 5,960,544 A | 10/1999 | Beyers |
| 5,964,758 A | 10/1999 | Dresden |
| 5,976,132 A | 11/1999 | Morris |
| 5,989,277 A | 11/1999 | LeMaire, III et al. |
| 5,997,565 A | 12/1999 | Inoue |
| 6,004,335 A | 12/1999 | Vaitekunas et al. |
| 6,010,516 A | 1/2000 | Hulka |
| 6,024,741 A | 2/2000 | Williamson et al. |
| 6,024,744 A | 2/2000 | Kese et al. |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,074,386 A | 6/2000 | Goble et al. |
| RE36,795 E | 7/2000 | Rydell |
| 6,083,223 A | 7/2000 | Baker |
| 6,086,586 A | 7/2000 | Hooven |
| 6,090,107 A | 7/2000 | Borgmeier et al. |
| 6,096,037 A | 8/2000 | Mulier et al. |
| 6,099,550 A | 8/2000 | Yoon |
| 6,102,909 A | 8/2000 | Chen et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,123,701 A | 9/2000 | Nezhat |
| H1904 H | 10/2000 | Yates et al. |
| 6,126,658 A | 10/2000 | Baker |
| 6,152,923 A | 11/2000 | Ryan |
| 6,162,220 A | 12/2000 | Nezhat |
| 6,174,309 B1 | 1/2001 | Wrublewski et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |

| | | |
|---|---|---|
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,302,424 B1 | 10/2001 | Gisinger et al. |
| 6,319,451 B1 | 11/2001 | Brune |
| 6,322,561 B1 | 11/2001 | Eggers et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,500,176 B1 | 12/2002 | Truckai et al. |
| 6,511,480 B1 | 1/2003 | Tetzlaff et al. |
| 6,514,252 B2 | 2/2003 | Nezhat et al. |
| 6,527,771 B1 | 3/2003 | Weadock et al. |
| 6,558,385 B1 | 5/2003 | McClurken et al. |
| 6,562,037 B2 | 5/2003 | Paton et al. |
| 6,585,735 B1 | 7/2003 | Frazier et al. |
| 6,602,252 B2 | 8/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 | 11/2003 | Ellman et al. |
| 6,656,177 B2 | 12/2003 | Truckai et al. |
| 6,660,072 B2 | 12/2003 | Chatterjee |
| 6,669,696 B2 | 12/2003 | Bacher et al. |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,860,880 B2 | 3/2005 | Treat et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,258 B2 | 2/2007 | Buysse et al. |
| 7,195,631 B2 | 3/2007 | Dumbauld |

| | | | | | | |
|---|---|---|---|---|---|---|
| D541,418 S | 4/2007 | Schechter et al. | | 2005/0107785 A1 | 5/2005 | Dycus et al. |
| 7,207,990 B2 | 4/2007 | Lands et al. | | 2005/0113818 A1 | 5/2005 | Sartor et al. |
| D541,938 S | 5/2007 | Kerr et al | | 2005/0113826 A1 | 5/2005 | Johnson et al. |
| 7,223,265 B2 | 5/2007 | Keppel | | 2005/0113827 A1 | 5/2005 | Dumbauld et al. |
| 7,232,440 B2 | 6/2007 | Dumbauld et al. | | 2005/0113828 A1 | 5/2005 | Shields et al. |
| 7,241,288 B2 | 7/2007 | Braun | | 2005/0119655 A1 | 6/2005 | Moses et al. |
| 7,241,296 B2 | 7/2007 | Buysse et al. | | 2005/0149017 A1 | 7/2005 | Dycus |
| 7,252,667 B2 | 8/2007 | Moses et al. | | 2005/0187547 A1 | 8/2005 | Sugi |
| 7,255,697 B2 | 8/2007 | Dycus et al. | | 2005/0197659 A1 | 9/2005 | Bahney |
| 7,267,677 B2 | 9/2007 | Johnson et al. | | 2005/0203504 A1 | 9/2005 | Wham et al. |
| 7,270,660 B2 | 9/2007 | Ryan | | 2005/0240179 A1 | 10/2005 | Buysse et al. |
| 7,270,664 B2 | 9/2007 | Johnson et al. | | 2006/0052778 A1 | 3/2006 | Chapman et al. |
| 7,276,068 B2 | 10/2007 | Johnson et al. | | 2006/0064085 A1 | 3/2006 | Schechter et al. |
| 7,300,435 B2 | 11/2007 | Wham et al. | | 2006/0074417 A1 | 4/2006 | Cunningham et al. |
| 7,303,557 B2 | 12/2007 | Wham et al. | | 2006/0079888 A1 | 4/2006 | Mulier et al. |
| 7,314,471 B2 | 1/2008 | Holman | | 2006/0079890 A1 | 4/2006 | Guerra |
| 7,329,256 B2 | 2/2008 | Johnson et al. | | 2006/0116675 A1 | 6/2006 | McClurken et al. |
| 7,329,257 B2 | 2/2008 | Kanehira et al. | | 2006/0129146 A1 | 6/2006 | Dycus et al. |
| D564,662 S | 3/2008 | Moses et al. | | 2006/0161150 A1 | 7/2006 | Keppel |
| 7,342,754 B2 | 3/2008 | Fitzgerald et al. | | 2006/0167450 A1 | 7/2006 | Johnson et al. |
| 7,344,268 B2 | 3/2008 | Jigamian | | 2006/0167452 A1 | 7/2006 | Moses et al. |
| 7,367,976 B2 | 5/2008 | Lawes et al. | | 2006/0173452 A1 | 8/2006 | Buysse et al. |
| 2002/0049442 A1 | 4/2002 | Roberts et al. | | 2006/0189980 A1 | 8/2006 | Johnson et al. |
| 2002/0107517 A1 | 8/2002 | Witt et al. | | 2006/0189981 A1 | 8/2006 | Dycus et al. |
| 2002/0188294 A1 | 12/2002 | Couture et al. | | 2006/0190035 A1 | 8/2006 | Hushka et al. |
| 2003/0014052 A1 | 1/2003 | Buysse et al. | | 2006/0217709 A1 | 9/2006 | Couture et al. |
| 2003/0014053 A1 | 1/2003 | Nguyen et al. | | 2006/0224158 A1 | 10/2006 | Odom et al. |
| 2003/0018331 A1 | 1/2003 | Dycus et al. | | 2006/0259036 A1 | 11/2006 | Tetzlaf et al. |
| 2003/0018332 A1 | 1/2003 | Schmaltz et al. | | 2006/0264922 A1 | 11/2006 | Sartor et al. |
| 2003/0032956 A1 | 2/2003 | Lands et al. | | 2006/0264931 A1 | 11/2006 | Chapman et al. |
| 2003/0069571 A1 | 4/2003 | Treat et al. | | 2006/0271038 A1 | 11/2006 | Johnson et al. |
| 2003/0078578 A1 | 4/2003 | Truckai et al. | | 2006/0287641 A1 | 12/2006 | Perlin |
| 2003/0109875 A1 | 6/2003 | Tetzlaff et al. | | 2007/0016182 A1 | 1/2007 | Lipson et al. |
| 2003/0114851 A1 | 6/2003 | Truckai et al. | | 2007/0016187 A1 | 1/2007 | Weinberg et al. |
| 2003/0139741 A1 | 7/2003 | Goble et al. | | 2007/0043352 A1 | 2/2007 | Garrison et al. |
| 2003/0139742 A1 | 7/2003 | Wampler et al. | | 2007/0043353 A1 | 2/2007 | Dycus et al. |
| 2003/0158549 A1 | 8/2003 | Swanson | | 2007/0055231 A1 | 3/2007 | Dycus et al. |
| 2003/0181910 A1 | 9/2003 | Dycus et al. | | 2007/0060919 A1 | 3/2007 | Isaacson et al. |
| 2003/0199869 A1 | 10/2003 | Johnson et al. | | 2007/0062017 A1 | 3/2007 | Dycus et al. |
| 2003/0216732 A1 | 11/2003 | Truckai et al. | | 2007/0074807 A1 | 4/2007 | Guerra |
| 2003/0229344 A1 | 12/2003 | Dycus et al. | | 2007/0078456 A1 | 4/2007 | Dumbauld et al. |
| 2004/0030330 A1 | 2/2004 | Brassell et al. | | 2007/0078458 A1 | 4/2007 | Dumbauld et al. |
| 2004/0030332 A1 | 2/2004 | Knowlton et al. | | 2007/0078459 A1 | 4/2007 | Johnson et al. |
| 2004/0064151 A1 | 4/2004 | Mollenauer | | 2007/0088356 A1 | 4/2007 | Moses et al. |
| 2004/0078035 A1 | 4/2004 | Kanehira et al. | | 2007/0106295 A1 | 5/2007 | Garrison et al. |
| 2004/0082952 A1 | 4/2004 | Dycus et al. | | 2007/0106297 A1 | 5/2007 | Dumbauld et al. |
| 2004/0087943 A1 | 5/2004 | Dycus et al. | | 2007/0118111 A1 | 5/2007 | Weinberg |
| 2004/0115296 A1 | 6/2004 | Duffin | | 2007/0118115 A1 | 5/2007 | Artale et al. |
| 2004/0116924 A1 | 6/2004 | Dycus et al. | | 2007/0142833 A1 | 6/2007 | Dycus et al. |
| 2004/0122423 A1 | 6/2004 | Dycus et al. | | 2007/0142834 A1 | 6/2007 | Dumbauld |
| 2004/0143263 A1 | 7/2004 | Schechter et al. | | 2007/0156139 A1 | 7/2007 | Schechter et al. |
| 2004/0147925 A1 | 7/2004 | Buysse et al. | | 2007/0156140 A1 | 7/2007 | Baily |
| 2004/0162557 A1 | 8/2004 | Tetzlaff et al. | | 2007/0173811 A1 | 7/2007 | Couture et al. |
| 2004/0176762 A1 | 9/2004 | Lawes et al. | | 2007/0173814 A1 | 7/2007 | Hixson et al. |
| 2004/0193153 A1 | 9/2004 | Sarter et al. | | 2007/0179499 A1 | 8/2007 | Garrison |
| 2004/0225288 A1 | 11/2004 | Buysse et al. | | 2007/0203485 A1 | 8/2007 | Keppel |
| 2004/0236325 A1 | 11/2004 | Tetzlaff et al. | | 2007/0213706 A1 | 9/2007 | Dumbauld et al. |
| 2004/0236326 A1 | 11/2004 | Schulze et al. | | 2007/0213707 A1 | 9/2007 | Dumbauld et al. |
| 2004/0243125 A1 | 12/2004 | Dycus et al. | | 2007/0213708 A1 | 9/2007 | Dumbauld et al. |
| 2004/0249371 A1 | 12/2004 | Dycus et al. | | 2007/0213712 A1 | 9/2007 | Buysse et al. |
| 2004/0249374 A1 | 12/2004 | Tetzlaff et al. | | 2007/0255279 A1 | 11/2007 | Buysse et al. |
| 2004/0250419 A1 | 12/2004 | Sremcich et al. | | 2007/0260235 A1 | 11/2007 | Podhajsky |
| 2004/0254573 A1 | 12/2004 | Dycus et al. | | 2007/0260238 A1 | 11/2007 | Guerra |
| 2004/0260281 A1 | 12/2004 | Baxter, III et al. | | 2007/0260241 A1 | 11/2007 | Dalla Betta et al. |
| 2005/0004568 A1 | 1/2005 | Lawes et al. | | 2007/0260242 A1 | 11/2007 | Dycus et al. |
| 2005/0004570 A1 | 1/2005 | Chapman et al. | | 2007/0265616 A1 | 11/2007 | Couture et al. |
| 2005/0021025 A1 | 1/2005 | Buysse et al. | | 2008/0004616 A1 | 1/2008 | Patrick |
| 2005/0021026 A1 | 1/2005 | Baily | | 2008/0009860 A1 | 1/2008 | Odom |
| 2005/0021027 A1 | 1/2005 | Shields et al. | | 2008/0015575 A1 | 1/2008 | Odom et al. |
| 2005/0096645 A1 | 5/2005 | Wellman et al. | | 2008/0021450 A1 | 1/2008 | Couture |
| 2005/0101951 A1 | 5/2005 | Wham et al. | | 2008/0033428 A1 | 2/2008 | Artale et al. |
| 2005/0101952 A1 | 5/2005 | Lands et al. | | 2008/0039835 A1 | 2/2008 | Johnson et al. |
| 2005/0107784 A1 | 5/2005 | Moses et al. | | 2008/0045947 A1 | 2/2008 | Johnson et al. |

| | | | |
|---|---|---|---|
| 2008/0058802 A1 | 3/2008 | Couture et al. | |
| 2008/0082100 A1 | 4/2008 | Orton et al. | |

FOREIGN PATENT DOCUMENTS

| | | |
|---|---|---|
| DE | 2415263 | 10/1975 |
| DE | 2627679 | 1/1977 |
| DE | 4303882 | 8/1994 |
| DE | 29616210 | 1/1997 |
| DE | 19608716 | 4/1997 |
| DE | 19751106 | 5/1998 |
| DE | 19751108 | 5/1999 |
| EP | 0364216 A1 | 4/1990 |
| EP | 518230 A1 | 12/1992 |
| EP | 0 541 930 B1 | 5/1993 |
| EP | 0572131 | 12/1993 |
| EP | 584787 A1 | 3/1994 |
| EP | 0589453 A2 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 853922 A1 | 7/1998 |
| EP | 0887046 A3 | 1/1999 |
| EP | 0923907 A1 | 6/1999 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1301135 A | 4/2003 |
| EP | 1472984 A1 | 11/2004 |
| EP | 1527747 A2 | 5/2005 |
| EP | 1530952 A1 | 5/2005 |
| EP | 1535581 A2 | 6/2005 |
| EP | 1609430 A1 | 12/2005 |
| EP | 1632192 A1 | 3/2006 |
| EP | 1645238 A1 | 4/2006 |
| EP | 1645240 A2 | 4/2006 |
| EP | 1707143 A1 | 10/2006 |
| GB | 2214430 A | 6/1989 |
| GB | 2213416 | 8/1989 |
| JP | 501068 | 9/1984 |
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001128990 A2 | 5/2001 |
| JP | 2001029356 A2 | 2/2006 |
| SU | 401367 | 10/1973 |
| WO | WO89/00757 | 1/1989 |
| WO | WO 92/04873 | 4/1992 |
| WO | WO 92/06642 | 4/1992 |
| WO | WO 94/08524 A | 4/1994 |
| WO | WO94/20025 | 9/1994 |
| WO | WO 95/02369 | 1/1995 |
| WO | WO95/07662 | 3/1995 |
| WO | WO 95/07662 | 3/1995 |
| WO | WO95/15124 | 6/1995 |
| WO | WO96/05776 | 2/1996 |
| WO | WO 96/13218 | 9/1996 |
| WO | WO 97/00646 | 1/1997 |
| WO | WO 97/00647 | 1/1997 |
| WO | WO97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/40857 | 8/1999 |
| WO | WO 99/51158 | 10/1999 |
| WO | WO 99/66850 A | 12/1999 |
| WO | WO 00/24330 | 5/2000 |
| WO | WO00/24331 | 5/2000 |
| WO | WO 00/41638 | 7/2000 |
| WO | WO00/47124 | 8/2000 |
| WO | WO 00/53112 | 9/2000 |
| WO | WO 01/17448 A | 3/2001 |
| WO | WO 01/54604 | 8/2001 |
| WO | WO 02/07627 | 1/2002 |
| WO | WO02/07627 | 1/2002 |
| WO | WO 02/067798 A1 | 9/2002 |
| WO | WO 02/080783 | 10/2002 |
| WO | WO02/080783 | 10/2002 |
| WO | WO02/080784 | 10/2002 |
| WO | WO 02/080784 | 10/2002 |
| WO | WO 02/080785 | 10/2002 |
| WO | WO02/080785 | 10/2002 |
| WO | WO 02/080786 | 10/2002 |
| WO | WO02/080786 | 10/2002 |
| WO | WO02/080793 | 10/2002 |
| WO | WO 02/080793 | 10/2002 |
| WO | WO 02/080794 | 10/2002 |
| WO | WO02/080794 | 10/2002 |
| WO | WO 02/080795 | 10/2002 |
| WO | WO 02/080796 | 10/2002 |
| WO | WO02/080797 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO02/081170 | 10/2002 |
| WO | WO 03/090630 A3 | 11/2003 |
| WO | WO 2004/032776 A1 | 4/2004 |
| WO | WO2004/032777 | 4/2004 |
| WO | WO 2004/032777 | 4/2004 |
| WO | WO 2004/052221 | 6/2004 |
| WO | WO 2004/073488 A2 | 9/2004 |
| WO | WO2004/073490 | 9/2004 |
| WO | WO 2004/073490 | 9/2004 |
| WO | WO2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 A1 | 1/2005 |
| WO | WO2005/004735 | 1/2005 |
| WO | WO 2005/110264 | 11/2005 |

OTHER PUBLICATIONS

Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.

Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Levy et al. "Use of a New Energy-based Vessel Ligation Device During Vaginal Hysterectomy" Int'l Federation of Gynecology and Obstetrics (FIGO) World Congress 1999.
Crawford et al. "Use of the LigaSure Vessel Sealing System in Urologic Cancer Surger". Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.
"Reducing Needlestick Injuries in the Operating Room" Sales/Product Literature 2001.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.

W. Scott Helton, "LigaSure Vessel Sealing System: Revolutionary Hemostasis Product for General Surgery" Sales/Product Literature 1999.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With The LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing For Hemostasis During Gynecologic Surgery" Sales/Product Literature 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.
Joseph Ortenberg "LigaSure System Used in Laparoscopic 1st and 2nd Stage Orchiopexy" Innovations That Work, Nov. 2002.
Koyle at al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640.
Int'l Search Report PCT/US98/23950.
Int'l Search Report PCT/US99/24869.
Int'l Search Report PCT/US01/11218.
Int'l Search Report PCT/US01/11340.
Int'l Search Report PCT/US01/11420.
Int'l Search Report PCT/US02/01890.
Int'l Search Report PCT/US02/11100.
Int'l Search Report PCT/US04/03436.
Int'l Search Report PCT/US04/13273.
Int'l Search Report PCT/US04/15311.
Int'l Search Report EP 98944778.
Int'l Search Report EP 98958575.
Int'l Search Report EP 04027314.
Int'l Search Report EP 04027479.
Int'l Search Report EP 04027705.
Int'l Search Report EP 04013772.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.

* cited by examiner

MAGNETIC CLOSURE MECHANISM FOR HEMOSTAT

CROSS-REFERENCE TO RELATED APPLICATION

The present application claims benefit of and priority to U.S. Provisional Application Ser. No. 60/620,805 filed on Oct. 21, 2004, the entire disclosure of which is incorporated herein by reference.

BACKGROUND

The present disclosure relates to a closure mechanism for hemostat devices. More particularly, the present disclosure relates to a magnetic closure mechanism for hemostat devices.

TECHNICAL FIELD

A hemostat device is a surgical instrument which relies on mechanical action between its jaws to grasp, clamp, constrict and seal vessels or tissue. Such devices are commonly used in open, endoscopic or laparoscopic surgical procedures. Electrosurgical hemostats (open or endoscopic) utilize both mechanical clamping action and electrical energy to affect hemostasis by heating tissue and blood vessels to coagulate, cauterize or seal tissue.

Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Vessel sealing or tissue sealing is a recently-developed technology which utilizes a unique combination of radiofrequency energy, pressure and gap control to effectively seal or fuse tissue between two opposing jaw members or sealing plates. Vessel or tissue sealing is more than "cauterization" which is defined as the use of heat to destroy tissue (also called "diathermy" or "electrodiathermy") and vessel sealing is more than "coagulation" which is defined as a process of desiccating tissue wherein the tissue cells are ruptured and dried. "Vessel sealing" is defined as the process of liquefying the collagen, elastin and ground substances in the tissue so that it reforms into a fused mass with significantly-reduced demarcation between the opposing tissue structures.

In order to effectively "seal" tissue or vessels, two predominant mechanical parameters must be accurately controlled: 1) the pressure applied to the vessel or tissue; and 2) the gap distance between the conductive tissue contacting surfaces (electrodes). As can be appreciated, both of these parameters are affected by the thickness of the tissue being sealed. Accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal.

With respect to smaller vessels or tissue, the pressure applied becomes less relevant and the gap distance between the electrically conductive surfaces becomes more significant for effective sealing. In other words, the chances of the two electrically conductive surfaces touching during activation increases as the tissue thickness and the vessels become smaller.

Typically and when utilizing standard hemostats, the surgeon would have to determine the appropriate amount of pressure needed to seal the tissue and maintain that specific amount of pressure while sealing the tissue. Obviously, in this instance, the effectiveness of the seal would depend on the skill of the surgeon during activation. To assist the surgeon in maintaining the correct pressure required to seal the given tissue, many recently developed devices utilize some sort of latch or ratchet that will lock the hemostat device into a certain position thereby keeping a constant predetermined pressure on the tissue being sealed. Maintaining a constant pressure on the tissue is one of the important parameters for effective tissue sealing. For other types of tissue treatments, i.e., coagulation and cauterization, maintaining consistent pressures within a certain range is less relevant to successful tissue treatment.

Some of the known simpler latches are easy to use and inexpensive to manufacture however, they are limited in that they are not adjustable. Therefore these latches can only be used to apply a set or definitive amount of pressure regardless of the tissue being sealed or the pressure required to effectively seal the tissue. In certain circumstances such as vessel sealing this design is effective since the application of the correct amount of pressure is an important parameter when sealing vessels. However, for cauterization or coagulation purposes, the surgeon may desire an adjustable instrument. Some highly technical latches have been made that are adjustable however these devices usually contain many parts, require additional steps to use and are expensive to manufacture. For example, a series of progressive ratchet-like mechanical interfaces may be employed to incrementally adjust the ratchet pressures. Obviously, this design feature adds to the overall complexity of the instrument and may not be suited for sealing vessels if the pressures associated with the successive ratchet positions fall outside the preferred pressure ranges for sealing.

Thus, there exists a need to develop a hemostat device which is simple, reliable and inexpensive to manufacture and which effectively seals tissue and vessels and which allows a surgeon to simply latch the device into a closed position with a predetermined closure pressure which is effective for vessel sealing.

SUMMARY

The present disclosure relates to a hemostat that is generally used for grasping and/or sealing tissue. The hemostat includes a housing which has a shaft extending distally therefrom and an end effector assembly distally attached to the shaft. The housing is also connected to a pair of first and second handles which are operatively connected to the end effector assembly.

The hemostat further includes a magnetic closure mechanism. The magnetic closure mechanism has a first magnet of a first magnetic potential and a second magnet of a second magnetic potential. The first magnet is connected to the first handle and the second magnet is connected to the second handle. The first and second magnets are securely engageable with one another when the handles are moved from a first spaced configuration to a second closer position.

In one embodiment the first and second magnets are selectively removable and interchangeable. The first and second magnets are attached to the pair of first and second handles using any means known to those skilled in the art. Some examples include, but are not limited to, snaps, grooves, screws, pins, and combinations of these means.

In another embodiment, the first and second magnets are each covered by a polymeric covering. Any polymeric covering known to those skilled in the art may be used to cover each of the first and second magnets. Preferably, the polymeric covering is made from a natural polymer, a synthetic polymer or combinations of both. It is envisioned that the polymeric covering may not only protect the magnets from damage resulting from direct contact, but may also assist in increasing or decreasing the magnetic attraction between the first and second magnets.

The present disclosure also relates to a hemostat which includes a housing which has a shaft extending distally therefrom and an end effector assembly distally attached to the shaft. The end effector assembly includes opposing first and second jaw members. The jaw members are adapted to connect to an electrical energy source such that the jaw members can selectively apply electrical energy through tissue held therebetween. A pair of first and second handles is connected to the housing and the pair of handles is also operatively connected to the end effector assembly. At least one of the handles is moveable relative to the other handle to effectively actuate the end effector assembly. The hemostat also includes a magnetic closure mechanism that maintains a closure pressure between the opposing jaw members within a predefined pressure range. The magnetic closure mechanism includes a first magnet which has a first magnetic potential and a second magnet which has a second magnetic potential. The first magnet is connected to the first handle and the second magnet is connected to the second handle. The first and second magnets are securely engageable with one another when the handles are moved from a first spaced configuration to a second closer position.

The present disclosure further relates to a hemostat which has first and second shafts that are pivotably mounted for movement relative to one another from a first spaced configuration to a second closer configuration. Each of the first and second shafts has respective jaw members at a distal end thereof and respective handles at a proximal end thereof. The jaw members are disposed in opposing relation relative to one another. The hemostat also includes a magnetic closure mechanism that maintains a closure pressure between the opposing jaw members within a predefined pressure range. The magnetic closure mechanism has a first magnet of a first magnetic potential and a second magnet of a second magnetic potential. The first magnet and the second magnet are securely engageable with one another when the first handle and the second handle are moved from a first spaced configuration to a second closer configuration.

BRIEF DESCRIPTION OF THE DRAWINGS

Various embodiments of the subject instrument are described herein with reference to the drawings wherein.

DETAILED DESCRIPTION

Figures 1A, 1B:
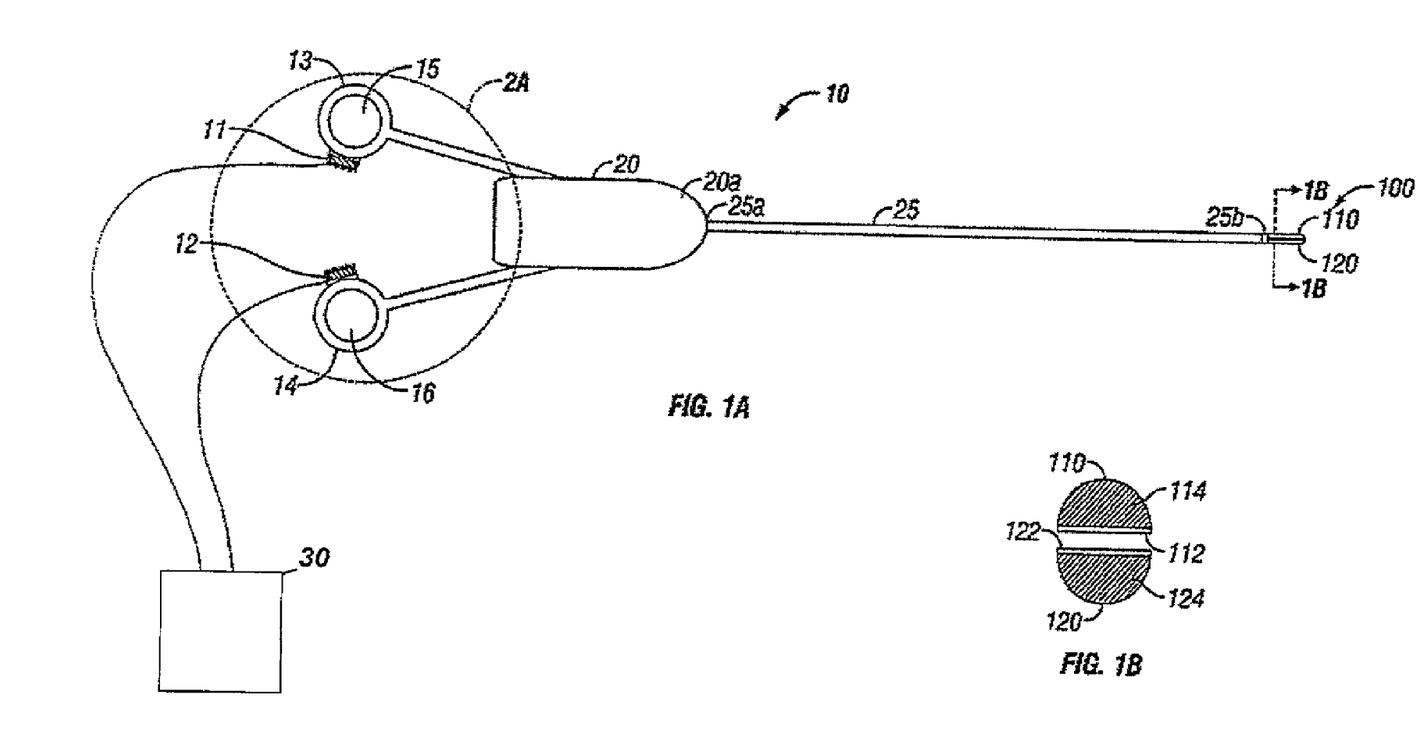
FIG. 1A is a side view of a hemostat having a magnetic closure mechanism according to the present disclosure.
FIG. 1B is an enlarged view taken along line 1B-1B of FIG. 1A.

Referring now to FIGS. 1A-1B, there is shown a hemostat device 10 which includes a housing 20, a shaft 25 and a pair of first and second handles 13 and 14, respectively. Handles 13 and 14 includes a magnetic closure mechanism 17. Shaft 25 is connected to a distal end 20a of housing 20 and handles 13 and 14 extend proximally therefrom. The term "proximal", as is traditional, will refer to the end of the hemostat device 10 which is closer to the user, while the term "distal" will refer to the end which is further from the user.

The shaft 25 includes a proximal end 25a which engages housing 20 at distal end 20a and shaft 25 includes a distal end 25b which engages an end effector assembly 100. End effector assembly 100 includes a pair of opposing jaw members 110 and 120 which each include an outer insulative housing 114 and 124, respectively, and an inwardly disposed tissue engaging surface 112 and 122, respectively. As explained in more detail below, movement of the handles 13 and 14 from a first position (FIG. 2A) to a second position (FIG. 2B) correspondingly moves the jaw members 110 and 120 from an open position to a closed position for grasping tissue.

Figure 2A:
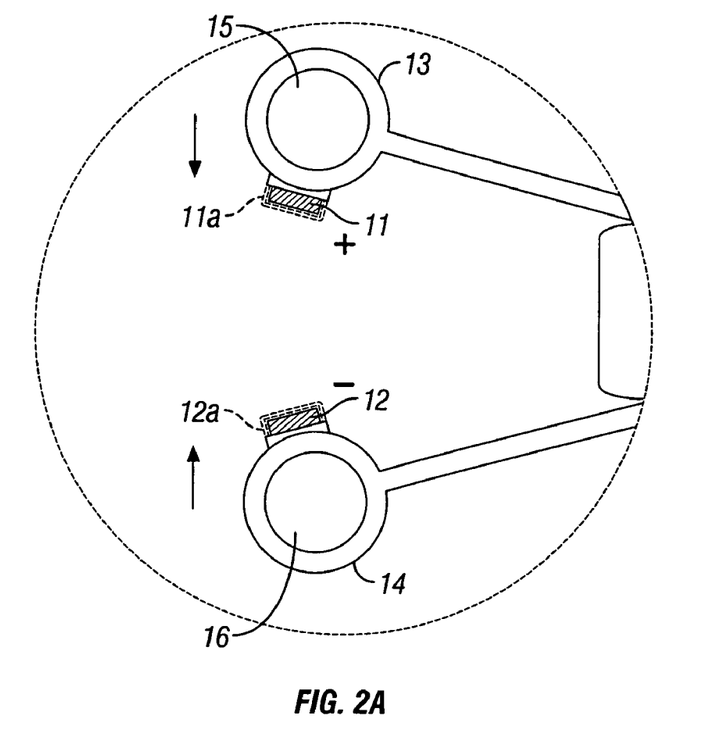
FIG. 2A is an enlarged, side view of the handles of the hemostat of FIG. 1A shown in an open configuration.
Figure 2B:
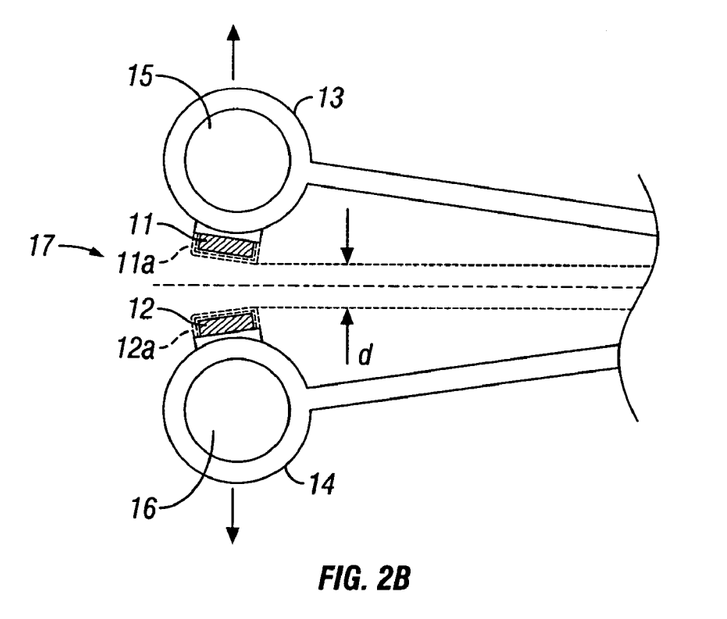
FIG. 2B is an enlarged side view of the handles of the hemostat of FIG. 1A the handles being approximated to a closed position.

The handles 13 and 14, which preferably lay in the same plane, are movable and may be brought together (closed) or separated from each other (opened) as shown by the arrows in FIGS. 2A and 2B. Movement of the handles 13 and 14 also facilitates similar movement of the magnets 11 and 12 and the jaws 110 and 120.

Each of the first and second handles 13 and 14 contains a finger hole 15 and 16, respectively, which allows a user to place his/her fingers into the holes 15 and 16 to grip and facilitate movement of the handles 13 and 14. The finger holes 15 and 16 may include one or more ergonomically friendly features which enhance the tactile feel and grip for the user to facilitate actuation of the forceps 10. Such features may include, raised protuberances, rubber inserts, scallops and gripping surfaces and the like.

The opposing jaw members 110 and 120 may be configured to perform a variety of known surgical tasks but are preferably configured to seal tissue and as such are adapted to connect to an electrosurgical generator (not shown). Preferably, jaw members 110 and 120 and include one or more stop members (not shown) on or adjacent the tissue surfaces 112 and 122 to enhance sealing. Commonly-owned U.S. patent application Ser. No. 10/471,818 disclosed a variety of stop members which may be utilized for this purpose, the entire contents of which being incorporated by reference herein.

Since different tissue types offer different amounts of resistance force to the opposing jaw members 110 and 120, the opposing jaw members 110 and 120 and the magnetic closure mechanism 17 are configured to apply and maintain a consistent closure pressure between opposing tissue surfaces 112 and 122 to effect sealing. Preferably, the jaw members 110 and 120 of the magnetic closure mechanism 17 apply a closure pressure in the range of about 3 kg/cm$^2$ to about 16 kg/cm$^2$. The required closure pressure is generated by the magnetic attraction of a set of first and second magnets 11 and 12 and translated through the set of handles 13 and 14 and the shaft 25 to the opposing jaw members 110 and 120. As can be appreciated housing 20 may include one or more mechanically assisting elements which help generate the required closure pressure within the above-identified range, e.g., gears of varying ratios or spring elements. As such the magnets 11 and 12 may not necessarily need to be configured to include an attractive force which generates all of the closure pressure to the jaw members 110 and 120.

Figure 3A:
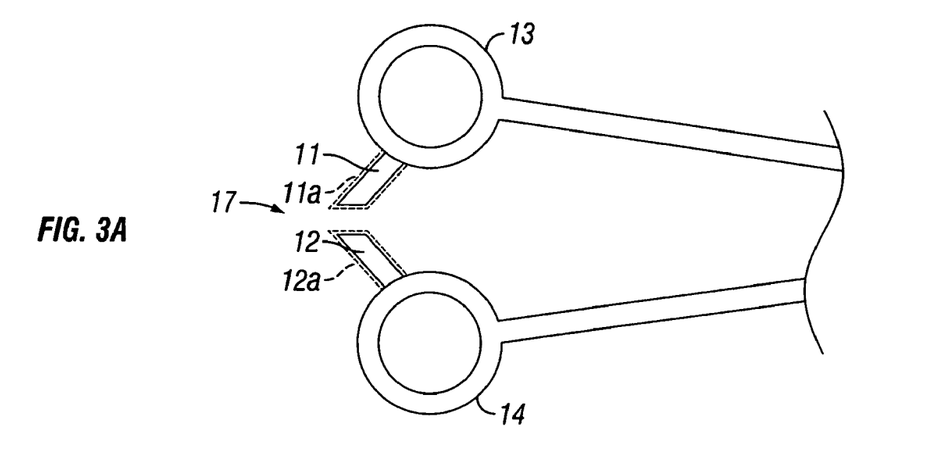
FIGS. 3A-3C are enlarged, side views of the handles showing magnets of varying configurations.

The magnets 11 and 12, which are attached to handles 13 and 14 respectively, may vary in size, shape, thickness, polarity and location on the handles 13 and 14, as long as the magnets 11 and 12 lay on the same plane or axis thereby allowing the magnets 11 and 12 to become magnetically engaged upon closure of the handles 13 and 14. Some examples include, but are not limited, to those shown in FIGS. 3A-C.

Figure 3B:
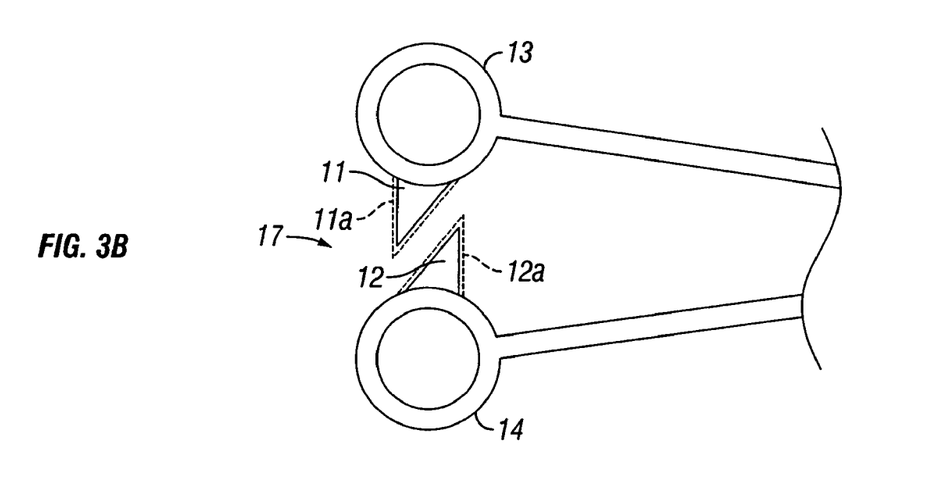
Figure 3C:
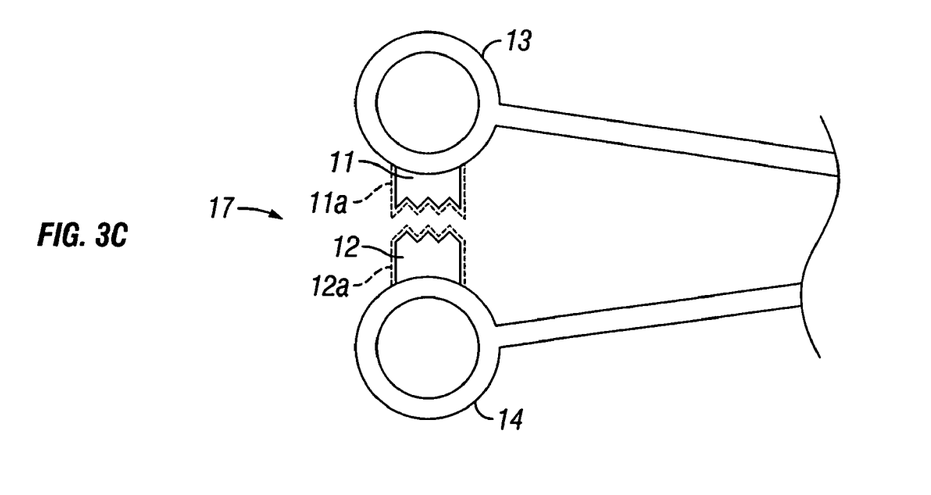

For example, it is envisioned that magnets 11 and 12 may be configured to have a variety of different cross sections which include circular, square-like, octagonal, triangular etc. which vary in magnetic force depending upon a particular purpose. It is further envisioned that the particular shape of the magnet(s) may be dimensioned to enhance closure of the handles 13 and 14 relative to one another, i.e., which is the angle the magnets 11 and 12 and are oriented on the handles 13 and 14 and the shape of the magnets 11 and 12 may be configured to vary the attractive magnetic force as the handles 13 and 14 close. For example, the magnets 11 and 12 show in FIGS. 3A-3C will tend to have variable degrees of magnetic attraction due to the respective position of each magnet 11 and 12 on handles 13 and 14 as well as each magnets 11 and 12 respective shape. For example, the magnets 11 and 12 shown in FIG. 3B will tend to lessen the distance that the user needs to move the handles 13 and 14 before magnetic attraction facilitates closing. The magnets 11 and 12 of FIG. 3B are envisioned to have a greater surface area of magnetic force which will help maintain the closure pressure within the above-working range. Likewise, the mechanically engaging teeth of magnets 11 and 12 of FIG. 3C will also help maintain closure pressures.

It is also envisioned that the angle at which the magnets 11 and 12 approach each other as the handles 13 and 14 come together, may vary depending upon the size, shape, thickness, polarity and location of the magnets 11 and 12. More particularly, as seen in FIG. 2B, depending upon the magnetic attraction force, the distance between the magnets 11 and 12 (represented by the letter "d") and the degree of attraction between magnets 11 and 12 can be varied to adjust the angular displacement to which the user needs to initiate the closure or unclosure force. As the angle increases or decreases, the magnetic attraction force between the two magnets 11 and 12 similarly increases or decreases. Likewise, the shape of the magnets 11 and 12 varies the magnetic fields associated with each of the same which can facilitate closing of the handles 13 and 14.

As seen in FIG. 2A, the magnets 11 and 12 each possess a different polarity. The greater the difference in polarity the stronger the magnetic attraction force between the two magnets 11 and 12. The magnetic attraction force must be at least slightly greater than the resisting force translated from the opposing jaws 110 and 120 to the handles 13 and 14 to facilitate mating engagement of the magnets 11 and 12. As mentioned above, various mechanical components, e.g., springs and gears (not shown) may be employed within housing 20 to decrease the amount of magnetic energy needed to maintain the closing pressure within the preferred range.

Also seen in FIG. 2A, the magnets 11 and 12 may be covered by a polymeric covering 11a and 12a depicted in phantom representation. The polymeric coverings 11a and 12a prevent the magnets 11 and 12 from actually contacting each other. Instead the polymeric coverings 11a and 12a are designed to make contact with each other. This design reduces the actual physical wear and tear on the magnets 11 and 12 essentially prolonging the life of the magnets 11 and 12.

The polymeric coverings 11a and 12a may be made from any material known to those skilled in the art. Some examples include natural and synthetic polymers. Preferably the polymeric covers 11a and 12a are made of the same material used to make the handles 13 and 14 or the hemostat device 10.

The polymeric coverings 11a and 12a not only protect the magnets 11 and 12 from physical damage but also help prevent the magnets 11 and 12 from becoming matingly engaged when the magnets 11 and 12 are placed or forced off-plane or off-axis. For example, a user of the hemostat device 10 with the handles 13 and 14 magnetically latched together or in the closed position may easily separate or open the handles 13 and 14 by simply forcing the handles 13 and 14 and magnets 11 and 12 slightly off-plane or off-axis. If, for example, a thicker coat of polymer material is disposed on the sides of magnets 11 and 12, this off-axis positioning significantly decreases magnetic attraction between the magnets 11 and 12 thereby allowing the handles 13 and 14 to move away from each other to open the opposing jaw members 110 and 120 in a simpler fashion.

It is envisioned that the magnets 11 and 12, whether covered or uncovered, may possess a predetermined polarity thereby creating a predetermined magnetic attraction force between the two magnets 11 and 12. More particularly, the hemostat device 10 may possess a predetermined magnetic attraction force which is specifically measured to overcome the resistance force of a certain type of tissue to be sealed such that when the handles 13 and 14 are closed, the opposing jaw members 110 and 120 maintain the tissue under a working pressure between about 3 kg/cm$^2$ to about 16 kg/cm$^2$.

It is also envisioned that magnets 11 and 12 that possess a predetermined polarity may be removable and/or interchangeable thereby allowing the user of the hemostat device 10 to strengthen or weaken the magnetic attraction force as needed to overcome the resistive force of the specific tissue being sealed. More particularly, the magnets 11 and 12 may be attached to the handle 13 and 14 via snaps, grooves, screws, pins, and the like to accomplish this purpose.

In another embodiment, the magnets may be electromagnets. More particularly, the hemostat device 10 may be connected to an additional power source 30, such as electrical current, a battery, and the like, which can regulate the polarity of the individual electromagnets thereby regulating the magnetic attraction force between the two electromagnets. By using electromagnets, the user is able to alter the magnetic attraction force between the electromagnets at the simple flip of a switch. This alteration creates a hemostat device 10 capable of being adjusted as needed during the tissue sealing procedure to assuredly maintain the working pressure. A sensor 240, or the like, may be employed on the jaw members 110 and 120 to measure the pressure to assure that it is within a desired range prior to initiating the electrical energy.

In yet another embodiment, the hemostat can also be a standard open forceps for grasping tissue. Commonly-owned U.S. patent application Ser. Nos. 10/248,562 and 10/962,116 describe a variety of other similar instruments which may be utilized for grasping tissue, the entire contents of which are incorporated by reference herein.

Figure 4:
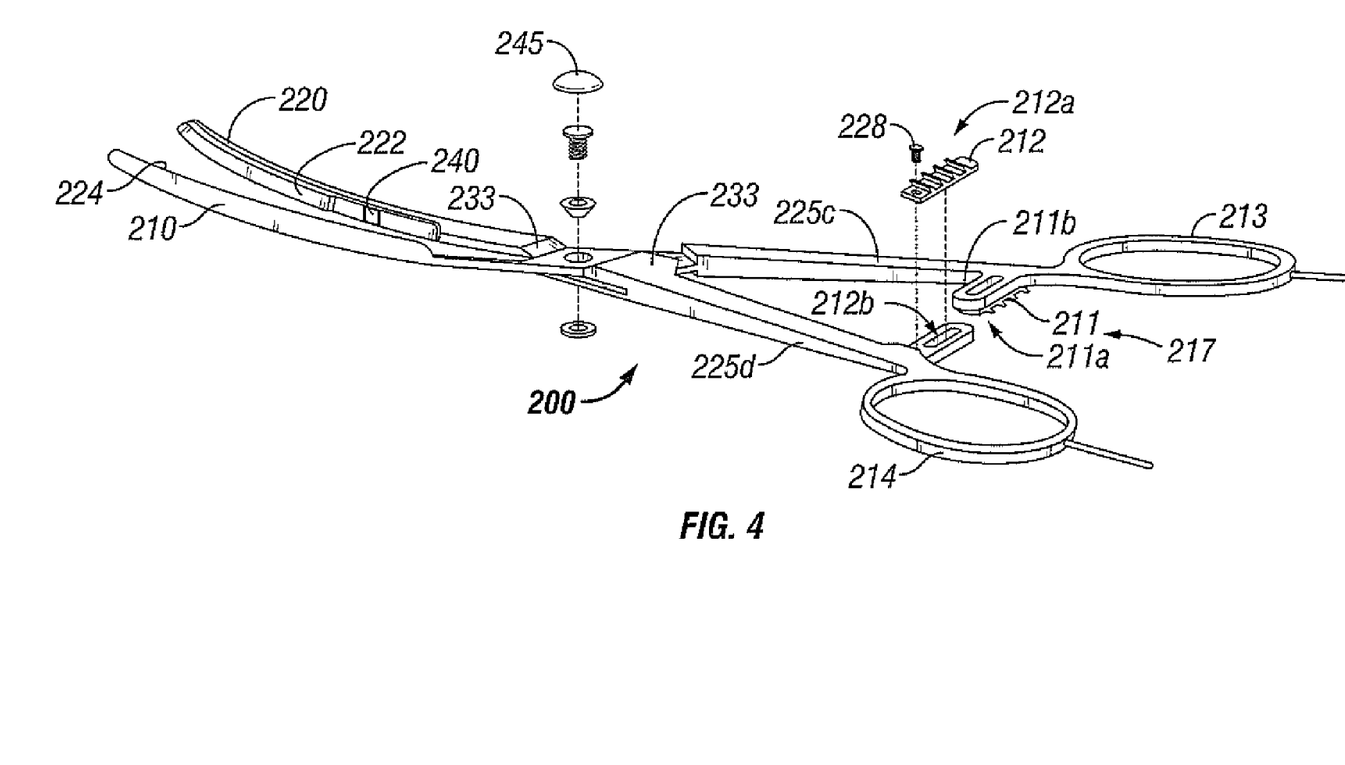
FIG. 4 is a perspective view of an open forceps for use with the presently disclosed magnetic closure mechanism.

As shown in FIG. 4, hemostat 200 has first and second shafts 225c, 225d that are pivotably mounted 233 for movement relative to one another about pivot assembly 245 from a first spaced configuration to a second closer configuration. Each shaft 225c, 225d has a jaw member 210, 220 at a distal end thereof and jaw members 210, 220 are disposed in opposing relation relative to one another. Each jaw member may also possess an inwardly disposed tissue engaging surface 222, 224. A pair of first and second handles 213, 214 is attached to the proximal end of shafts 225c, 225d. First handle 213 is attached to first shaft 225c and second handle 214 is attached to second shaft 225d. The hemostat also includes magnetic closure mechanism 217 that maintains a closure pressure between opposing jaw members 210, 220 within the above-identified predefined pressure range or another predefined pressure range to accomplish a particular surgical purpose. Magnetic closure mechanism 217 has first magnet 211 of a first magnetic potential connected to first handle 213 and second magnet 212 of a second magnetic potential connected to second handle 214. First magnet 211 and second magnet 212 are securely engageable with one another when first handle 213 and second handle 214 are moved from a first spaced configuration to a second closer configuration.

Also shown in FIG. 4, first magnet 211 and second magnet 212 each include assistant elements, for example, ratchet surfaces 211a and 212a. Each ratchet surface, e.g., 211a, extends from the handle 213 towards the other ratchet 212a on the other handle 214 such that the inner facing surfaces of each ratchet 211a and 212a abut one another when the end effectors 210 and 220 are moved from the open position to the closed position. Each ratchet surface 211a and 212a includes a plurality of flanges 211b and 212b, respectively, which project from the inner facing surface of each ratchet surface 211a and 212a such that the ratchet surfaces 211a and 212a can interlock in at least one position. In an embodiment shown in FIG. 4, the ratchets 211a and 212a interlock, i.e., bias each other in a spring-like manner, at several different positions. In this configuration, each ratchet position may hold a specific, i.e., constant, strain energy in the shafts 225c and 225d which, in turn, transmit a specific force to the end effectors 210 and 220 and, thus, the electrodes 222 and 224.

It is envisioned that magnets 211, 212 may be removable and/or interchangeable. As shown in FIG. 4, magnets 211, 212 may be attached to handles 213, 214 via screw 228 or other attachment mechanisms known in the art. In addition, magnets of varying potential may be utilized for varying surgical purposes. Further and as indicated above, the magnets may be coupled to an energy source to increase the magnetic forces at closure to maintain a desired closure force.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

The invention claimed is:

1. An electrosurgical instrument, comprising:
a housing having a shaft extending distally therefrom, said shaft having an end effector assembly attached at a distal end thereof, said end effector assembly including a pair of opposing jaw members, each opposing jaw member having an electrically conductive sealing surface that communicates electrosurgical energy through tissue held therebetween, said electrically conductive sealing surface of each jaw member being adapted to communicate with a power source;
a pair of first and second handles connected to the housing and operatively connected to the end effector assembly, at least one of said handles moveable relative to the other said handles to effectively actuate the end effector assembly; and
a magnetic closure mechanism including a first variable electromagnet having a first magnetic polarity connected to said first handle and a second variable electromagnet having a second magnetic polarity connected to said second handle, said first and second variable electromagnets being securely engageable with one another by a variable magnetic attraction force when said handles are moved from a first spaced configuration to a second closer configuration, wherein said power source is configured to regulate said first and second magnetic polarities of the first and second electromagnets to vary the magnetic attraction force between the first and second electromagnets, thus providing and maintaining a working pressure between said opposing jaw members.

2. The electrosurgical instrument according to claim 1, wherein said end effector assembly includes opposing first and second jaw members and said magnetic closure mechanism maintains a closure pressure between opposing jaw members within a predefined pressure range.

3. The electrosurgical instrument according to claim 2, wherein at least one of said jaw members includes at least one stop member which controls a distance between opposing jaw members.

4. The electrosurgical instrument according to claim 2, wherein said predefined pressure range ranges from about 3 kg/cm$^2$ to about 16 kg/cm$^2$.

5. The electrosurgical instrument according to claim 4, further comprising:
a sensor coupled to said jaw members, wherein said sensor measures said working pressure exerted by said jaw members and communicates with said power source to regulate said first and second magnetic polarities of the first and second electromagnets, such that said working pressure exerted by said jaw members is within said predefined pressure range prior to initiating said electrosurgical energy.

6. The electrosurgical instrument according to claim 1, wherein said first handle and said second handle are moveable relative to one another in the same plane.

7. The electrosurgical instrument according to claim 1, wherein at least one of said handles includes at least one ergonomically friendly feature to facilitate handling, said ergonomically friendly feature selected from the group consisting of raised protuberances, rubber inserts, scallops and gripping surfaces.

8. The electrosurgical instrument according to claim 1, wherein the shape of said first magnet and said second magnet are selected from the group consisting of circular, square-like, rectangular, and polygonal.

9. The electrosurgical instrument according to claim 1, wherein said first magnet and said second magnet are configured to include mechanically engaging teeth.

10. The electrosurgical instrument according to claim 1, wherein the said first magnet and said second magnet are each covered by a polymeric covering.

11. The electrosurgical instrument according to claim 10, wherein said polymeric covering is a natural polymer, synthetic polymer or combinations thereof.

12. The electrosurgical instrument according to claim 1, wherein said first magnet and said second magnet include adjustable magnetic polarities.

13. The electrosurgical instrument according to claim 1, wherein said first magnet and said second magnet are selectively removable and interchangeable.

14. The electrosurgical instrument according to claim 13, wherein said first magnet and said second magnet are attached to said pair of first and second handles using at least one means selected from the group consisting of snaps, grooves, screws, pins, and combinations thereof.

15. The electrosurgical instrument according to claim 1, wherein the magnets are electromagnets.

16. The electrosurgical instrument according to claim 1, wherein said housing includes a mechanically assisting element to help generate a greater closure pressure.

17. The electrosurgical instrument according to claim 1, wherein said mechanically assisting element includes at least one spring.

* * * * *